US009913931B2

(12) United States Patent
Åberg et al.

(10) Patent No.: US 9,913,931 B2
(45) Date of Patent: Mar. 13, 2018

(54) CEMENT-FORMING COMPOSITIONS, MONETITE CEMENTS, IMPLANTS AND METHODS FOR CORRECTING BONE DEFECTS

(71) Applicant: OssDsign AB, Uppsala (SE)

(72) Inventors: Jonas Åberg, Uppsala (SE); Thomas Engstrand, Uppsala (SE); Håkan Engqvist, Östhammar (SE)

(73) Assignee: OSSDSIGN AB, Uppsala (SE)

( * ) Notice: Subject to any disclaimer, the term of this patent is extended or adjusted under 35 U.S.C. 154(b) by 22 days.

(21) Appl. No.: 14/649,543

(22) PCT Filed: Dec. 16, 2013

(86) PCT No.: PCT/IB2013/061002
§ 371 (c)(1),
(2) Date: Jun. 3, 2015

(87) PCT Pub. No.: WO2014/091469
PCT Pub. Date: Jun. 19, 2014

(65) Prior Publication Data
US 2015/0328368 A1    Nov. 19, 2015

Related U.S. Application Data

(60) Provisional application No. 61/737,355, filed on Dec. 14, 2012.

(51) Int. Cl.
*C04B 28/34* (2006.01)
*A61L 27/42* (2006.01)
(Continued)

(52) U.S. Cl.
CPC .......... *A61L 27/425* (2013.01); *A61F 2/2846* (2013.01); *A61L 27/12* (2013.01); *A61F 2230/0073* (2013.01); *A61L 2430/02* (2013.01)

(58) Field of Classification Search
CPC .................. C04B 28/34; C04B 28/344; C04B 2111/00836; A61L 27/425; A61L 27/12;
(Continued)

(56) References Cited

U.S. PATENT DOCUMENTS

| 5,152,836 A | 10/1992 | Hirano et al. |
| 5,338,356 A | 8/1994  | Hirano et al. |

(Continued)

FOREIGN PATENT DOCUMENTS

| CN | 1919357 A   | 2/2007 |
| CN | 102089238 A | 7/2009 |

(Continued)

OTHER PUBLICATIONS

Legrand, AP; Sfihi, H.; Lequeux, N.; Lemaitre, J. "31P Solid-State NMR Study of the Chemical Setting Process of a Dual-Paste Injectable Brushite Cements". Apr. 13, 2009.*

(Continued)

*Primary Examiner* — Helene Klemanski
(74) *Attorney, Agent, or Firm* — Porter Wright Morris & Arthur LLP

(57) ABSTRACT

A calcium phosphate monetite cement-forming composition comprises a monetite-forming calcium-based precursor powder and from 3 to 30 wt %, based on the weight of the precursor powder, of dicalcium pyrophosphate powder. Monetite cements formed form such compositions may be used in implants for correcting bone defects. Methods for bone defect repair employ implants formed from such monetite cements and slow implant resorption and/or improve in vivo bone induction in a patient.

21 Claims, 1 Drawing Sheet

(51) Int. Cl.
*A61L 27/12* (2006.01)
*A61F 2/28* (2006.01)

(58) Field of Classification Search
CPC .............. A61L 2430/02; A61F 2/2846; A61F 2230/0073
USPC .................................................. 106/690, 691
See application file for complete search history.

(56) References Cited

U.S. PATENT DOCUMENTS

| | | | |
|---|---|---|---|
| 5,605,713 | A | 2/1997 | Boltong |
| 5,683,667 | A | 11/1997 | Fulmer et al. |
| 5,782,971 | A | 7/1998 | Constantz et al. |
| 5,783,217 | A | 7/1998 | Lee et al. |
| 6,117,456 | A | 9/2000 | Lee et al. |
| 6,206,957 | B1 | 3/2001 | Wenz et al. |
| 6,338,810 | B1 | 1/2002 | Carpena |
| 6,425,949 | B1 * | 7/2002 | Lemaitre ............ A61L 24/0084 106/35 |
| 6,521,246 | B2 | 2/2003 | Sapieszko et al. |
| 6,642,285 | B1 | 11/2003 | Bohner et al. |
| 6,733,582 | B1 | 5/2004 | Bohner et al. |
| 6,863,899 | B2 | 3/2005 | Koblish et al. |
| 6,905,516 | B1 | 6/2005 | Lemaitre et al. |
| 6,991,803 | B2 | 1/2006 | Sapieszko et al. |
| 7,118,705 | B2 | 10/2006 | Lin |
| 7,175,858 | B2 | 2/2007 | Constantz et al. |
| 7,252,841 | B2 | 8/2007 | Constantz et al. |
| 7,318,841 | B2 | 1/2008 | Tofighi et al. |
| 7,351,280 | B2 | 4/2008 | Khairoun et al. |
| 7,407,542 | B2 | 8/2008 | Lemaitre et al. |
| 7,473,312 | B2 | 1/2009 | Barralet et al. |
| 7,501,018 | B2 | 3/2009 | Engqvist et al. |
| 7,754,246 | B2 | 7/2010 | Mosley et al. |
| 8,591,645 | B2 | 11/2013 | Engqvist et al. |
| 8,709,149 | B2 | 4/2014 | Engqvist et al. |
| 2003/0082232 | A1 | 5/2003 | Lee et al. |
| 2003/0199615 | A1 | 10/2003 | Chaput et al. |
| 2006/0239884 | A1 | 10/2006 | Chane-Ching et al. |
| 2006/0263443 | A1 | 11/2006 | Chow et al. |
| 2007/0092856 | A1 | 4/2007 | Chow et al. |
| 2007/0189951 | A1 | 8/2007 | Constantz et al. |
| 2008/0027455 | A1 | 1/2008 | Bondeville |
| 2008/0028992 | A1 | 2/2008 | Lee et al. |
| 2008/0187571 | A1 | 8/2008 | Clineff et al. |
| 2008/0206300 | A1 | 8/2008 | Bohner et al. |
| 2009/0022771 | A1 | 1/2009 | Lynn et al. |
| 2009/0220475 | A1 | 9/2009 | Bohner et al. |
| 2010/0095870 | A1 | 2/2010 | Insley et al. |
| 2010/0269736 | A1 | 10/2010 | Chow et al. |
| 2010/0303888 | A1 | 12/2010 | Barralet et al. |
| 2011/0014244 | A1 | 1/2011 | Sapieszko et al. |
| 2011/0152195 | A1 | 6/2011 | O'Mahony et al. |
| 2011/0158963 | A1 | 6/2011 | Font Perez et al. |
| 2012/0058152 | A1 | 3/2012 | Garcia de Castro Andrews et al. |
| 2013/0138114 | A1 | 5/2013 | Lin et al. |

FOREIGN PATENT DOCUMENTS

| | | | | |
|---|---|---|---|---|
| CN | 102316911 | A | | 1/2012 |
| EP | 543765 | A1 | | 5/1993 |
| EP | 1023032 | B1 | | 1/2002 |
| EP | 936929 | B1 | | 6/2004 |
| EP | 1380313 | B1 | | 5/2005 |
| EP | 1298103 | B1 | | 5/2011 |
| JP | 1-100049 | A | | 4/1989 |
| WO | 00/07639 | A1 | | 2/2000 |
| WO | 02/11781 | A1 | | 2/2002 |
| WO | 03/024316 | A2 | | 3/2003 |
| WO | 2004/093734 | A2 | | 11/2004 |
| WO | 2005/074453 | A2 | | 8/2005 |
| WO | 2005/077049 | A2 | | 8/2005 |
| WO | 2007/047921 | A2 | | 4/2007 |
| WO | 2009/077210 | A1 | | 6/2009 |
| WO | WO 2009077210 | A1 * | 6/2009 | .......... A61L 24/0015 |
| WO | 2010/092001 | A1 | | 8/2010 |
| WO | 2011/009635 | A1 | | 1/2011 |
| WO | 2011/112145 | A1 | | 9/2011 |

OTHER PUBLICATIONS

Calcium phosphate cements: action of Mirtchi, Amir; Lemaitre, J. "Calcium phosphate cements: action of setting regulators on the properties of the beta-tricalcium phosphate-monocalcium phosphate cements". Nov. 1989.*
Han et al, Acta Biomaterialia, 5:3165-3177 (2009).
Desai et al, Advances in Bioceramics and Biocomposites II, Ceramic Engineering and Science Proceedings, vol. 27, Issue 6, Wereszczak et al, Editor, Wiley, pp. 61-69 (Nov. 2006).
Hirayama et al, Journal of Research of the National Institute of Standards and Technology, 113(6):311-320 (2008).
Bohner et al, J. Biomaterials, 26(33):6423-6429 (Nov. 1, 2005).
Xu et al, Journal of Materials Science: Materials in Medicine, 18(7):1345-1353 (Feb. 3, 2007).
Barralet et al, J. Biomaterials, 25(11):2197-2203 (2004).
Habraken et al, Advance Drug Delivery Reviews, 59(4-5):234-248 (Jun. 9, 2007).
Tamini et al, Acta Biomaterialia, 8(2):474-487 (Aug. 6, 2011).
Mirtchi et al, Biomaterials, 10(9):634-638 (1989).
Flautre et al, Journal of Biomedical Materials Research, 63(4):413-417 (2002).
Official Action dated Mar. 1, 2016 from corresponding Chinese Application No. 2013800656781.
Bohner et al, Journal of Materials Science: Material in Medicine, 11:111-116 (2000).
The Merck Index, 11th Edition, Budavari (ed.), p. 256 (1989).
Safronova et al, Inorganic Materials, 51(11):1177-1184 (2015).

* cited by examiner

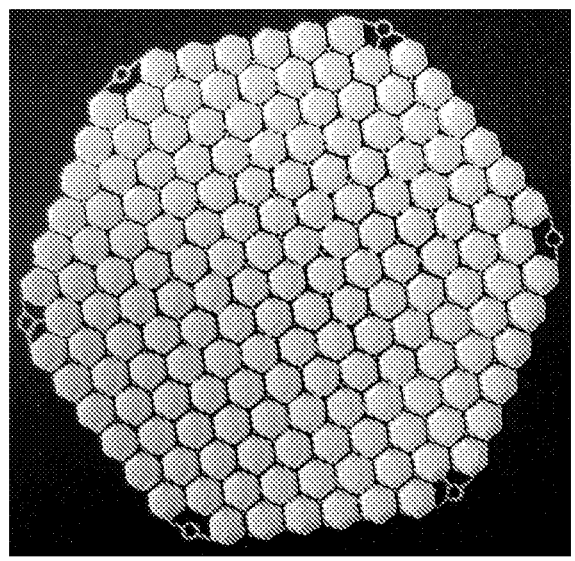

CEMENT-FORMING COMPOSITIONS, MONETITE CEMENTS, IMPLANTS AND METHODS FOR CORRECTING BONE DEFECTS

FIELD OF THE INVENTION

The invention relates to cement-forming compositions, monetite cements, implants, and methods for correcting bone defects.

BACKGROUND OF THE INVENTION

Bone tissue defects that cannot heal via tissue regeneration can be filled using autograph, allograph or synthetic scaffold materials. For large defects, e.g. defects in the cranium or in long bones, healing of bone defects can be especially difficult. A wealth of bioceramic formulations and delivery forms have been suggested for use as bone void filler materials. Examples of bone void fillers include cements, e.g. apatite and brushite based cements, and powders or granules, e.g. β-TCP and apatite powders and granules. Delivery forms include injectable forms and granules packed directly into an open bone defect. Injectable cements have been proposed both as premixed versions and as formulations to be mixed in the operating room. One major drawback with the current suggested material formulations is their relatively low bone induction capability. This is especially important in repair of large and complex bone defects, as in the cranium. Some bioceramic formulations which have been reported as having an ability to induce bone formation include hydroxyapatite (porous), biphasic calcium phosphate ceramics, tricalcium phosphate ceramic, calcium pyrophosphate and apatite cement formulations. In addition to these, bone induction capability of some calcium phosphate formulations has been very difficult to combine with a tailored resorption rate and a material handling technique that facilitates industrial use of the materials, e.g. in the operating room and/or for moulding of complex shapes.

Accordingly, there is an unmet need for a material that has a slow and optimal resorption rate in vivo and/or induces bone formation, and is easily handled in the operating room and/or when moulding complex shaped implants.

SUMMARY OF THE INVENTION

This invention is directed to compositions and methods that fulfil one or more of these unmet needs.

In one embodiment, the invention is directed to calcium phosphate monetite cement-forming compositions which comprise a monetite-forming calcium-based precursor powder and, optionally, a non-aqueous water-miscible liquid.

In one specific embodiment, the monetite-forming calcium-based precursor powder comprises monocalcium phosphate, β-tricalcium phosphate, and from 3 to 30 wt %, based on the weight of the precursor powder, of dicalcium pyrophosphate (also referred to herein as calcium pyrophosphate) powder, and a non-aqueous liquid is employed in the cement-forming composition. The powder to liquid (wt/vol) ratio in the composition is from about 1 to 7.

In a second specific embodiment, the monetite-forming calcium-based precursor powder comprises monocalcium phosphate, β-tricalcium phosphate, and from 3 to 30 wt %, based on the weight of the precursor powder, of dicalcium pyrophosphate and is adapted to be mixed with an aqueous liquid or exposed to an aqueous liquid to achieve hardening.

This invention is also directed to monetite cements formed form such calcium phosphate monetite cement-forming compositions and to monetite cements comprising from 3 to 30 wt % of dicalcium pyrophosphate.

This invention is also directed to implants comprising a monetite cement, wherein the monetite cement comprises from 3 to 30 wt % of dicalcium pyrophosphate. In a more specific embodiment, the implants comprise a wire or mesh and one or a plurality of ceramic tiles moulded on the wire or mesh, wherein the ceramic tiles are formed of a monetite cement comprising from 3 to 30 wt % of β-dicalcium pyrophosphate. In a specific embodiment, the wire or mesh is formed of titanium. In another embodiment, the implant is provided in the form of hardened granules which may be placed in a patient's body.

This invention is also directed to methods of correcting bone defects. In one embodiment, such methods comprise slowing implant resorption in a bone defect repair in a patient by providing the patient with an implant formed of a monetite cement comprising from 3 to 30 wt % of dicalcium pyrophosphate. In another embodiment, such methods comprise providing improved bone induction in a bone defect repair in a patient by providing the patient with an implant formed of a monetite cement comprising from 3 to 30 wt % of dicalcium pyrophosphate. In another embodiment, these methods employ β-dicalcium pyrophosphate.

This invention is also directed to implants which slow bone resorption and/or improve bone induction in a bone defect repair in a patient, wherein the implant is formed of a monetite composition comprising from 3 to 30 wt % of dicalcium pyrophosphate. In another embodiment, these implants employ β-dicalcium pyrophosphate.

The cement-forming compositions, cements, implants and methods of the invention are advantageous in that they provide implants which have optimal resorption rates in vivo and/or induce bone formation, and are easily handled in the operating room or when moulding complex shaped implants. These and additional embodiments and advantages of the invention will be more apparent in view of the Detailed Description.

BRIEF DESCRIPTION OF THE DRAWINGS

Various embodiments of the invention will be more fully understood in view of the drawing in which:

The FIGURE shows one embodiment of an implant structure according to the present invention.

DETAILED DESCRIPTION

The present invention is directed to calcium phosphate monetite cement-forming compositions, monetite-forming calcium phosphate-based precursor powders for forming monetite cements, and monetite cements. The invention is also directed to implants formed of monetite cements and methods for correcting bone defects with monetite cement implants.

The calcium phosphate monetite cement-forming compositions comprise a monetite-forming calcium-based precursor powder and optionally a non-aqueous water-miscible liquid. In one specific embodiment, the monetite-forming calcium-based precursor powder comprises monocalcium phosphate, which may be monocalcium phosphate monohydrate (MCPM) and/or anhydrous monocalcium phosphate (MCPA), β-tricalcium phosphate, and from 3 to 30 wt %, based on the weight of the precursor powder, of dicalcium pyrophosphate (also referred to herein as calcium pyrophosphate) powder. In a specific embodiment, the monocalcium phosphate and β-tricalcium phosphate are employed in a weight ratio of about 40:60 to 60:40.

In one specific embodiment, the monetite-forming calcium-based precursor powder comprises monocalcium phosphate, β-tricalcium phosphate and calcium pyrophosphate. In one embodiment, the precursor powder comprises from about 70 to 98 wt % of monocalcium phosphate and β-tricalcium phosphate combined and from 3 to 30 wt % of dicalcium pyrophosphate powder, based on the weight of the precursor powder. In specific embodiments, the monocalcium phosphate and β-tricalcium phosphate are employed in a weight ratio of about 40:60 to 60:40, or, more specifically, in a weight ratio of 45:55 to 52:48.

In one embodiment, the monetite cement-forming compositions comprise the precursor powder as described and a non-aqueous water-miscible liquid. The precursor powder to liquid (wt/vol, i.e., g/ml) ratio may be from about 1 to 7, or more specifically, from about 2 to 6 in the cement compositions, or from about 2.5 to about 5, or from about 3 to about 4.5, for better handling and mechanical strength. The non-aqueous liquid facilitates handling and use, without premature hardening of the cement-forming compositions. Examples of the non-aqueous water-miscible liquid employed in embodiments according to the invention include, but are not limited to, glycerol and related liquids, compounds and derivates (substances derived from non-aqueous water-miscible substances), substitutes (substances where part of the chemical structure has been substituted with another chemical structure) and the like. The purpose of the non-aqueous water-miscible liquid is to give a longer working time during the moulding of the implant or during injection in the operating room (if used as an injectable cement). Certain alcohols may also be suitable for use as such a liquid. In specific embodiments, the liquid is selected from glycerol, propylene glycol, poly(propylene glycol), poly(ethylene glycol) and combinations thereof.

In specific embodiments containing the non-aqueous liquid, the composition liquid may be entirely non-aqueous or may be partly aqueous, i.e., containing <20 vol % water, or less than 10 vol % water, in the mixing liquid.

In another embodiment, the calcium phosphate cement-forming compositions comprise a monetite-forming calcium-based precursor powder as described above and may be mixed with an aqueous liquid or exposed to an aqueous liquid to achieve hardening. The liquid can be water or a water-based mixture. In one embodiment, the precursor powder composition is chosen to obtain a setting time above about 30 minutes. The cement-forming precursor powder is mixed with and/or exposed to water to achieve setting of the cement. This can be conducted for producing pre-formed implants or at the time of surgery for in vivo setting of the cement.

In any of the precursor powder compositions as described herein, the monocalcium phosphate is monocalcium phosphate monohydrate (MCPM) and/or anhydrous monocalcium phosphate (MCPA). In specific embodiments, the monocalcium phosphate is acidic and has a pH of less than 6.0. In a more specific embodiment, a 0.1 g/ml saturated aqueous solution of the monocalcium phosphate has a pH less than 3.0. In a more specific embodiment, a 0.1 g/ml saturated aqueous solution of the MCPA and MCPM exhibits a pH of 2.5-2.8. In one embodiment, the monocalcium phosphate (MCP) consists essentially of MCPA, whereby significant amounts of MCPM, i.e., greater than about 25%, or greater than about 10%, or greater than about 5%, based on the weight of the monocalcium phosphate, are excluded.

In another embodiment, the monocalcium phosphate consists of MCPA. The MCPA does not contain any crystal water as is the case with mono calcium phosphate monohydrate.

In specific embodiments, the precursor powder compositions and/or the monetite cement compositions according to the invention comprise from 3 to 30 wt % of dicalcium pyrophosphate. In further embodiments, the dicalcium pyrophosphate comprises from 3 to 10 wt %, from 4 to 10 wt %, from 5 to 10 wt %, from 6 to 10 wt %, from 7 to 10 wt %, or from 8 to 10 wt %, of the precursor powder and/or the monetite composition. In further embodiments, the dicalcium pyrophosphate comprises from 3 to 5 wt %, or from 4 to 5 wt % of the precursor powder and/or the monetite composition.

In further embodiments, the dicalcium pyrophosphate comprises from 3 to 15 wt %, from 4 to 15 wt %, from 5 to 15 wt %, from 6 to 15 wt %, from 7 to 15 wt %, from 8 to 15 wt %, from 9 to 15 wt %, from 10 to 15 wt %, from 11 to 15 wt %, or from 12 to 15 wt %, of the precursor powder and/or the monetite composition. In further embodiments, the dicalcium pyrophosphate comprises from 3 to 20 wt %, from 4 to 20 wt %, from 5 to 20 wt %, from 6 to 20 wt %, from 7 to 20 wt %, from 8 to 20 wt %, from 9 to 20 wt %, from 10 to 20 wt %, from 11 to 20 wt %, from 12 to 20 wt %, or from 15 to 20 wt %, of the precursor powder and/or the monetite composition. In further embodiments, the dicalcium pyrophosphate comprises from 3 to 25 wt %, from 4 to 25 wt %, from 5 to 25 wt %, from 6 to 25 wt %, from 7 to 25 wt %, from 8 to 25 wt %, from 9 to 25 wt %, from 10 to 25 wt %, from 11 to 25 wt %, from 12 to 25 wt %, from 13 to 25 wt %, from 14 to 25 wt %, from 15 to 25 wt %, or from 20 to 25 wt %, of the precursor powder and/or the monetite composition. In further embodiments, the dicalcium pyrophosphate comprises from 4 to 30 wt %, from 5 to 30 wt %, from 6 to 30 wt %, from 7 to 30 wt %, from 8 to 30 wt %, from 9 to 30 wt %, from 10 to 30 wt %, from 11 to 30 wt %, from 12 to 30 wt %, from 13 to 30 wt %, from 14 to 30 wt %, from 15 to 30 wt %, from 16 to 30 wt %, from 17 to 30 wt %, from 18 to 30 wt %, from 19 to 30 wt %, from 20 to 30 wt %, from 21 to 30 wt %, from 22 to 30 wt %, from 23 to 30 wt %, from 24 to 30 wt %, or from 25 to 30 wt %, of the precursor powder and/or the monetite composition.

In any of the embodiments disclosed herein, the dicalcium pyrophosphate may comprise alpha-dicalcium pyrophosphate, beta-dicalcium pyrophosphate and/or gamma-calcium pyrophosphate. In specific embodiments, the dicalcium pyrophosphate comprises beta-dicalcium pyrophosphate. In other specific embodiments, the dicalcium pyrophosphate comprises alpha-dicalcium pyrophosphate. In other specific embodiments, the dicalcium pyrophosphate comprises gamma-dicalcium pyrophosphate.

The monetite cements contain a majority, i.e., greater than 50 wt %, of monetite. In specific embodiments, the monetite cements contain at least 55 wt %, at least 60 wt %, at least 65 wt %, at least 70 wt %, at least 75 wt %, at least 80 wt %, at least 85 wt %, or at least 90 wt %, monetite. In additional embodiments, the monetite cements contain a minor amount of β-tricalcium phosphate. In more specific embodiments, the monetite cements contain from about 1 to 15 wt %, 1 to 10 wt %, or 2 to 20 wt %, of β-tricalcium phosphate.

Thus, specific embodiments of the monetite cements described herein comprise greater than 70 wt % or greater than 80 wt % monetite, 1 to 15 wt % or 1 to 10 wt %

0-tricalcium phosphate, and 3 to 20 wt % or 3 to 15 wt % dicalcium pyrophosphate, or, more specifically, β-dicalcium pyrophosphate.

The composition may also include agents that facilitate a fast diffusion of water into the composition in situ, preferably non-ionic surfactants like Polysorbates. The amount of surfactant is preferably between 0.01 and 5 wt % of the powder composition, most preferably, 0.1-1 wt %.

In specific embodiments, salts may be dissolved into the liquid to obtain a fast or slower setting, e.g. citric acid, $H_3C_6H_5O_7$, disodium pyrophosphate, $Na_2H_2P_2O_7$, sulfuric acid, $H_2SO_4$, and/or phosphoric acid, $H_3PO_4$. The hardening can then be performed in a dry environment.

In specific embodiments, the mean grain size of the precursor powder is preferably below 100 micrometer, and more preferably below 30 micrometer as measured in the volumetric grain size mode. Generally, smaller grain sizes give higher mechanical strength than larger grain sizes. In other embodiments, the grain size of the powders ranges from less than 100 micrometer up to about 600 micrometer, i.e., the precursor powder contains powders of varying sizes spanning the indicated range.

The monetite cement-forming compositions as described herein can be delivered prehardened in the form of granules, custom ceramic solid shaped implants, or ceramic tiles on metal or polymer meshes as disclosed in WO 2011/112145 A1, incorporated herein by reference. The monetite cement-forming compositions as described herein can be also be delivered as a premixed injectable material that sets and hardens in vivo.

In one embodiment, the monetite cement-forming compositions are delivered prehardened in the form of granules. In a specific embodiment, the granules have a size in a range of from about 100 μm to 5 mm, or, more specifically, from about 100 μm to 3 mm, or from about 100 μm to 1 mm. Such granules may be used in various implant applications, one example of which is for cleft repair.

In one embodiment, in order to obtain a shapeable implant, the cement-forming compositions are moulded onto wires or mesh as shown in the FIGURE. Using a non-aqueous water-miscible liquid, using a mixture of water and a non-aqueous water-miscible liquid, or using only water, a monetite cement-forming composition as described herein is allowed to harden over portions of the wire or mesh to form a monetite cement mosaic implant, for example using a mould. In one embodiment, the cement-forming composition is hardened to form the monetite cement by placing the mould in a water-containing bath to expose the cement-forming composition to water. Once the cement is formed, the mosaic implant is released from the mould. After packing and sterilization, the mosaic implant is ready to be used. The FIGURE shows a plurality of tiles formed of hardened hydraulic cement composition (monetite cement) in a mosaic pattern moulded onto titanium mesh according to one embodiment of the invention.

Implants formed of the monetite cement as described herein may be employed in methods for correcting or repairing bone defects. A specific embodiment comprises slowing implant resorption in a bone defect repair in a patient. The methods comprise providing the patient with an implant formed of a monetite composition as described comprising from 3 to 30 wt % of dicalcium pyrophosphate, or, more specifically, β-dicalcium pyrophosphate. Advantageously, the resorption may be slowed such that less than 30%, less than 20% or less than 10% resorption occurs over a period of 6 months, 12 months, 18 months, 24 months, 30 months or 36 months, after implant in vivo.

Another specific embodiment comprises providing improved bone induction in a bone defect repair in a patient. These methods comprise providing the patient with an implant formed of a monetite composition as described comprising from 3 to 30 wt % of dicalcium pyrophosphate, or, more specifically, β-dicalcium pyrophosphate. Advantageously, bone induction may be improved after implant in vivo.

Implants formed of the monetite cements as described herein may be employed in methods for slowing implant resorption and/or methods for improving bone induction in a bone defect repair in a patient, wherein the patient is provided with an implant formed of a monetite composition as described comprising from 3 to 30 wt % of dicalcium pyrophosphate, or, more specifically, β-dicalcium pyrophosphate.

Various features of the invention are exemplified in the following examples.

EXAMPLE 1

Mosaic implants as generally shown in the FIGURE were manufactured using the manufacturing method described above by moulding a premixed acidic calcium phosphate cement onto titanium (Ti) wires. The mosaic implants were used in experimental clinical trials for the restoration of large cranial defects. To form the implants, wires were placed in a mould, which was then filled with the premixed acidic calcium phosphate cement-forming composition, and the composition was allowed to harden in water for at least 48 hours to form monetite cement.

Two cement formulations were experimentally tested in the clinic trial:

A first formulation comprised premixed acidic calcium phosphate cement consisting of β-tricalcium phosphate, monocalcium phosphate monohydrate and glycerol. The β-tricalcium phosphate and monocalcium phosphate monohydrate were mixed in a molar ratio of 1:1 and the glycerol was added to the powder to obtain a powder:liquid ratio of 3.5:1 g/ml. The cement was thoroughly mixed until a homogenous paste was formed. After hardening and sterilization by autoclave, the cement was found to consist mainly of monetite ($CaHPO_4$) (>98%) and minor amounts of brushite ($CaHPO_4$-$2H_2O$), determined using x-ray diffraction analysis.

A second formulation comprised premixed acidic calcium phosphate cement consisting of 7 wt % calcium pyrophosphate, β-tricalcium phosphate, monocalcium phosphate monohydrate and glycerol. The β-tricalcium phosphate and monocalcium phosphate monohydrate were mixed in a molar ratio of 1:1 and the glycerol was added to the powder to obtain a powder:liquid ratio of 3.9:1 g/ml. The cement was thoroughly mixed until a homogenous paste was formed. After hardening and sterilization by autoclave, the cement was found to consist of ~85 wt % monetite, 7 wt % β-tricalcium phosphate, 7% β-dicalcium pyrophosphate and small amounts of brushite, determined using x-ray diffraction analysis.

The implants where implanted in two large cranial defects and followed for resorption and bone formation using CT (both patients) and PET imaging (for patient treated with formulation containing calcium pyrophosphate). The bone defects were exposed through a standard bi-coronal cranial skin flap. The soft tissue covering the defects were predominantly fibrotic in nature due to previous injury and surgery. The sterilized ceramic implants (standard autoclaving) were cut and adjusted to a size of approximately 85×95 mm, fitted into the defect, and fixated by titanium plates and screws. Perioperative antibiotic prophylaxis (Cloxacilin, Stragen Nordic, Denmark) was given. A functional analysis on bone growth was performed by (18)F fluoride PET combined with CT scans. The analysis showed that the patient treated with a mosaic containing the first cement formulation (monetite) showed extensive (substantially 100%) ceramic resorption after 6 months, whereas the patient treated with the second formulation (monetite+calcium pyrophosphate) showed very little resorption. After 27 months, (18)F fluoride PET showed new bone formation for the patient treated with the second cement formulation, and at 36 months, (18)F fluoride PET showed less than 10% resorption of the cement.

This example shows that by adding of dicalcium pyrophosphate to the monetite cement formulation, a desirable slower implant resorption and/or improved bone induction can be achieved.

EXAMPLE 2

This example studied in vitro dissolution properties of monetite cements. Two calcium phosphate cement formulations were prepared. Formulation 1 comprised about 85 wt % monetite, 8 wt % beta-tricalcium phosphate, and 7 wt % beta calcium pyrophosphate. Formulation 2 comprised 100 wt % monetite. Hexagonal samples with a start weight of ~300-400 mg of each formulation were placed in Phosphate Buffered Saline (PBS) solution, pH 7.4 at 37° C. The samples were dried once a month and weighed to monitor the weight loss due to dissolution. The PBS was exchanged once a month.

Results: After 12 months, Formulation 1 had decreased 20% in weight whereas formulation 2 had decreased 30% in weight. Both of these formulations show undesirably fast in vitro resorption and do not lead one of ordinary skill in the art to see any improvement by including dicalcium pyrophosphate in a monetite cement. Thus, the in vivo results of Example 1 are very surprising and unexpected in view of this in vitro study, and this in vitro study does not provide any suggestion as to the significantly different in vivo results obtained in Example 1.

EXAMPLE 3

This example also studied in vitro dissolution properties. Monetite cement formulations with different monetite, beta-tricalcium phosphate (beta-TCP) and beta-calcium pyrophosphate (beta-CPP) contents as set forth in Table 1 were prepared. Hexagonal samples with a start weight of ~300-400 mg of each formulation were placed in Tris(hydroxymethyl)-aminomethane-HCl buffer solution, pH 7.4 at 37° C. The samples were dried and weighed once per week and the solution was renewed. The weight loss at 2 weeks is shown in Table 1.

TABLE 1

| Formulation | Monetite | Beta-CPP | Beta-TCP | Weight loss at 2 weeks |
|---|---|---|---|---|
| 1 | 88.0 | 0 | 10.5 | 12% |
| 2 | 78.8 | 3.2 | 16.8 | 11% |
| 3 | 76.4 | 5.5 | 16.6 | 10% |
| 4 | 71.5 | 7.6 | 192 | 13% |
| 5 | 67.8 | 9.7 | 21.3 | 14% |

All of these formulations show undesirably fast in vitro resorption and do not lead one of ordinary skill in the art to see any improvement by including dicalcium pyrophosphate in a monetite cement. Thus, the in vivo results of Example 1 are very surprising and unexpected in view of this in vitro study, and this in vitro study shows the in vivo results obtained in Example 1 are surprising and unexpected. The compressive strength of the monetite compositions having varying amounts of calcium pyrophosphate in the range of from 0 wt % to about 30 wt % were measured and showed that the calcium pyrophosphate content did not significantly alter the compressive strength.

In view of the in vitro studies described in Examples 2 and 3, the in vivo results of Example 1 wherein the monetite composition containing calcium pyrophosphate advantageously exhibits slow resorption and the monetite composition which did not contain calcium pyrophosphate was substantially completely resorbed in 6 months, are unexpected and surprising.

The examples and specific embodiments set forth herein are illustrative in nature only and are not to be taken as limiting the scope of the invention defined by the following claims. Additional specific embodiments and advantages of the present invention will be apparent from the present disclosure and are within the scope of the claimed invention.

What is claimed is:

1. A hardened monetite cement, comprising at least 70 wt % of monetite and from 3 to 30 wt % of β-dicalcium pyrophosphate.

2. The hardened monetite cement according to claim 1, comprising at least 80 wt % of monetite and from 3 to 20 wt % of β-dicalcium pyrophosphate.

3. The hardened monetite cement according to claim 1, further comprising β-tricalcium phosphate (β-TCP).

4. The hardened monetite cement according to claim 1, comprising at least 75 wt % of monetite, from 3 to 20 wt % of β-dicalcium pyrophosphate, and from 1 to 15 wt %, of β-tricalcium phosphate (β-TCP).

5. The hardened monetite cement according to claim 1, comprising at least 80 wt % of monetite, from 3 to 15 wt % of β-dicalcium pyrophosphate, and from 1 to 10 wt %, of β-tricalcium phosphate (β-TCP).

6. The hardened monetite cement according claim 1, having a resorption rate in vivo of less than 30% over 6 months.

7. The hardened monetite cement according claim 1, having a resorption rate in vivo of less than 30% over 12 months.

8. The hardened monetite cement according to claim 1, formed from a monetite-forming precursor powder comprising monocalcium phosphate, β-tricalcium phosphate (β-TCP), and from 3 to 30 wt %, based on the weight of the precursor powder, of β-dicalcium pyrophosphate, wherein the weight ratio of monocalcium phosphate and β-TCP is in a range of 40:60 to 60:40.

9. The hardened monetite cement according to claim 8, wherein the weight ratio of monocalcium phosphate and β-TCP is in a range of 45:55 to 52:48.

10. The hardened monetite cement according to claim 8, wherein the monocalcium phosphate is monocalcium phosphate monohydrate.

11. The hardened monetite cement according to claim 8, wherein the monetite-forming precursor powder comprises from 3 to 20 wt %, based on the weight of the precursor powder, of β-dicalcium pyrophosphate.

12. The hardened monetite cement according to claim 8, formed by mixing the monetite-forming precursor powder with a non-aqueous water miscible liquid selected from glycerol, propylene glycol, poly(propylene glycol), poly (ethylene glycol) and combinations thereof, in a powder to liquid ratio of from about 2.5 to 5, and exposing the mixture to an aqueous liquid.

13. The hardened monetite cement according claim 1, sterilized by autoclaving.

14. An implant comprising the hardened monetite cement of claim 1.

15. The implant according to claim 14, comprising a titanium wire or mesh and one or a plurality of cement tiles moulded on the wire or mesh, wherein the one or plurality of ceramic tiles comprise the hardened monetite cement.

16. The implant according to claim 14, wherein the hardened monetite cement comprises at least 75 wt % of monetite, from 3 to 20 wt % of β-dicalcium pyrophosphate, and from 1 to 15 wt %, of β-tricalcium phosphate (β-TCP).

17. The implant according to claim 14, wherein the hardened monetite cement comprises at least 80 wt % of monetite, from 3 to 15 wt % of β-dicalcium pyrophosphate, and from 1 to 10 wt %, of β-tricalcium phosphate (β-TCP).

18. The implant according to claim 14, wherein the hardened monetite cement has a resorption rate in vivo of less than 30% over 6 months.

19. The implant according to claim 14, wherein the hardened monetite cement has a resorption rate in vivo of less than 20% over 12 months.

20. A method of correcting a bone defect in a patient, the method comprising providing the patient with the implant of claim 14.

21. A monetite-forming precursor powder comprising monocalcium phosphate, β-tricalcium phosphate (β-TCP), and from 3 to 30 wt %, based on the weight of the precursor powder, of β-dicalcium pyrophosphate, wherein the weight ratio of monocalcium phosphate and β-TCP is in a range of 40:60 to 60:40.

\* \* \* \* \*